United States Patent [19]

Kobayashi et al.

[11] 3,943,238

[45] Mar. 9, 1976

[54] METHOD FOR THE PREPARATION OF MEDICINAL CAPSULES

[75] Inventors: Toshiyuki Kobayashi, Yokohama; Kensuke Sunazuka, Kawasaki; Takeshi Mayama, Chigasaki; Akira Okada, Zushi, all of Japan

[73] Assignee: Meija Seika Co., Ltd., Japan

[22] Filed: Oct. 29, 1973

[21] Appl. No.: 410,334

[30] Foreign Application Priority Data

Nov. 1, 1972  Japan............................. 47-108876

[52] U.S. Cl..................... 424/37; 424/36; 424/359
[51] Int. Cl.²........................ A61J 3/07; A61K 9/48
[58] Field of Search......................... 424/37, 36, 359

[56] References Cited
UNITED STATES PATENTS

| | | | |
|---|---|---|---|
| 650,760 | 5/1900 | Metcalf................................. | 424/37 |
| 671,804 | 4/1901 | Metcalf................................. | 424/37 |
| 2,990,333 | 6/1961 | Graham................................ | 424/37 |
| 3,456,051 | 7/1969 | Mima et al............................ | 424/37 |
| 3,493,652 | 2/1970 | Hartman.............................. | 424/94 |
| 3,639,259 | 2/1972 | Scarpelli.............................. | 424/37 X |

FOREIGN PATENTS OR APPLICATIONS 1,467,792  12/1968  Germany

OTHER PUBLICATIONS

Newton et al., J. Pharm. Pharmac. 23:452–453 (1971) "The Effect of Additives on the Release of Drug From Hard Gelatin Capsules."

Awe et al., Chem. Abst., 54:1801f(1960) "Formaldehyde–Casein As Tablet Disintegrant".

Tudermann et al., Chem. Abst., 55:2017a (1961) "Formaldehyde–Casein As Tablet Disintegrator".

*Primary Examiner*—Shep K. Rose
*Attorney, Agent, or Firm*—McGlew and Tuttle

[57] ABSTRACT

A method for the preparation of gelatin capsules having a good disintegrating property, in which a material selected from the group consisting of a protein, an amino acid, a substance having at least one amino group, an antioxidant, monobasic sodium phosphate, and the mixture thereof is added to the encapsulated contents.

1 Claim, No Drawings

METHOD FOR THE PREPARATION OF MEDICINAL CAPSULES

This invention relates to a method for the preparation of a gelatin capsule having a good disintegrating property.

It is well known that the disintegrating property of a gelatin capsule is generally lowered as time lapses. This tendency becomes more prominent especially when the capsule content includes the following materials: a reducing sugar such as glucose, mannose, lactose or the like, or a substance, including polyethylene glycol, which produces aldehydes gradually as time lapses; or a substance having a carbonyl group, such as aspirin, kitasamycin, maleic acid, maridomycin, midecamycin, phthalic acid, josamycin, carbomycin, spiramycin, succinic acid, erythromycin, oleandomycin, fumaric acid, cellulose acetate phthalate, hydroxypropyl-methylcellulose phthalate, polyvinyl acetate, diethylaminoacetate, and methylacrylate-methacrylic acid copolymer.

Conditions for the disintegration test of capsules are prescribed in Japanese Pharmacopeia or Japanese Standards of Antibiotic Products and the disintegrability is considered as an important factor in determining the utility of a capsule. Unless the capsule has a suitable disintegrating property, the medicine filled in the capsule can not give its effects in practical applications. The present inventors have conducted an extensive study for improving the disintegrating property of the gelatin capsule. Experiments revealed that it is almost impossible to prevent the gelatin capsule from the time-wise deterioration by resorting to a known method of using a disintegrator including calcium carboxymethylcellulose, crystal cellulose and corn starch, or a surface active agent which is employed singly or in combination with the said disintegrator.

According to the present invention, there is provided a method for the preparation of a gelatin capsule improved in disintegrating property, characterized by adding to a medicinal substance to be charged in the capsule an additive including: a protein such as casein, gelatin, collagen, gluten, skim milk, bean protein; diastase or the like; an amino acid such as arginine, histidine, lysine, tryptophan, glycine, ornithine, or the like; a substance having at least one amino group such as glucosamine, nicotinamide, urea or the like; an antioxidant such as sodium bisulfite, sodium hydrosulfite; sodium phosphate, monobasic; or the mixture thereof, whereby time-wise deterioration in disintegrating property of the gelatin capsule is well prevented. Though not critical, the amount of the additive to be added is preferred to be above 0.1 % by weight based on the medicinal content of the capsule.

The present invention will be particularly illustrated by the following examples.

EXAMPLE 1

20 parts by weight of lysine hydrochloride was suitably mixed with 70 parts by weight of starch and 10 parts by weight of polyethylene glycol in a mixer. The mixture was filled by means of a filling machine in the No. 1 hard gelatin capsules in an amount of 350 mg/capsule. These capsules were maintained at 60°C for 2 weeks for the determination of disintegrability. The test results are shown below in comparison with the capsules without additives. (The liquid used for the determination was the No. 1 liquid prescribed in Japanese Pharmacopeia.)

| Additive | Disintegration time of Capsules | |
|---|---|---|
| | Immediately after produced | After maintained at 60°C for 2 weeks |
| Lysine hydrochloride | 3 – 5 min | 4 – 5 min |
| Nil | 3 – 5 min | 15 – 17 min |

EXAMPLE 2

Example 1 was repeated except that the mixture was replaced by that of 5 parts by weight of nicotinamide and 95 parts by weight of glucose and the resultant hard capsules were maintained at 60°C for 1 week. The test results are shown below. (The test liquid used for the determination was the No. 1 liquid prescribed in Japanese Pharmacopeia.)

| Additive | Disintegration time of Capsules | |
|---|---|---|
| | Immediately after produced | After maintained at 60°C for 1 week |
| Nicotinamide | 2 – 3 min | 3 – 5 min |
| Nil | 2 – 3 min | 15 – 16 min |

EXAMPLE 3

25 parts by weight of casein was mixed with 70 parts by weight of midecamycin and 5 parts by weight of hydroxypropylmethylcellulose phthalate. The resultant mixture was filled in the No. 2 hard gelatin capsules in an amount of 250 mg per capsule in the same manner as in Example 1. The resultant capsules were maintained at 40°C for 2 months and then immersed in an artificial gastric juice as prescribed in Japanese Standards of Antibiotic products for testing the disintegrability thereof. Capsules without additive were used as control. This process was repeated except that 25 parts by weight of isolated bean protein powder was used instead of casein. The test results are shown below.

| Additive | Disintegration Time of Capsules | |
|---|---|---|
| | Immediately after produced | After maintained at 40°C for 2 months |
| Casein | 2 – 5 min | 2 – 6 min |
| Isolated bean protein | 2 – 6 min | 2 – 10 min |
| Nil | 2 – 6 min | 19 – 21 min |

EXAMPLE 4

0.1 part by weight of sodium bisulfite was mixed with 99.9 parts by weight of kitasamycin. The resultant mixture was filled in the No. 5 hard gelatin capsules in an amount of 70 mg/capsule in the same manner as in Example 1. Kitasamycin alone was also filled in the capsules in the same manner as mentioned above. The resultant filled capsules were maintained at 60°C for 2 weeks and then immersed in water for determining the disintegrating property thereof. The tests results are shown below.

| Additive | Disintegration Time of Capsules | |
|---|---|---|
| | Immediately after produced | After maintained at 60°C for 2 weeks |
| Sodium bisulfite | 2 – 4 min | 4 – 5 min |

-continued

| Additive | Disintegration Time of Capsules | |
|---|---|---|
| | Immediately after produced | After maintained at 60°C for 2 weeks |
| Nil | 2 – 4 min | 18 – 19 min |

EXAMPLE 5

20 parts by weight of gelatin was mixed with 80 parts by weight of acetylspiramycin. The mixture was filled in the No. 2 hard gelatin capsules in an amount of 260 mg/capsule. Furthermore, acetylspiramycin alone was filled in the same manner as mentioned above. The resultant two kinds of capsules were maintained at 40°C for 2 months and then immersed in water for determining the disintegrability thereof. The test results are shown below.

| Additive | Disintegration time of Capsules | |
|---|---|---|
| | Immediately after produced | After maintained at 40°C for 2 months |
| Gelatin | 3 – 4 min | 5 – 8 min |
| Nil | 3 – 4 min | 17 – 20 min |

EXAMPLE 6

5 parts by weight of diastase and 5 parts by weight of lysine hydrochloride were mixed with 85 parts by weight of glucose and 5 parts by weight of maleic acid. The mixture was filled in No. 1 hard gelatin capsules in an amount of 360 mg/capsule. A mixture of 85 parts by weight of glucose and 5 parts by weight of maleic acid was further separately filled in the capsules in the same manner as mentioned above. The two kinds of the resultant capsules were maintained at 60°C for 1 week and immersed in the No. 1 liquid prescribed in Japanese Pharmacopeia for determining the disintegrating property thereof. The test results are shown below.

| Additive | Disintegration Time of Capsules | |
|---|---|---|
| | Immediately after produced | After maintained at 60°C for 1 week |
| Diastase and Lysine hydrochloride | 2 – 4 min | 5 – 6 min |
| Nil | 3 – 4 min | 18 – 22 min |

EXAMPLE 7

15 parts by weight of gelatin and 15 parts by weight of sodium phosphate, monobasic, were mixed with 70 parts by weight of midecamycin. The mixture was filled in the No. 2 hard gelatin capsules in an amount of 250 mg/capsule in the same manner as in Example 1. Furthermore, midecamycin alone was filled in the capsules in the same manner as mentioned above. The two kinds of the resultant capsules were maintained at 60°C for 2 weeks and immersed in an artificial gastric juice prescribed in Japanese Standards of Antibiotic Products for determining the disintegrability of the capsules. The test results are shown below.

| Additive | Disintegration Time of Capsules | |
|---|---|---|
| | Immediately after produced | After maintained at 60°C for 2 weeks |
| Gelatin and sodium phosphate, monobasic | 3 – 4 min | 3 – 7 min |
| Nil | 3 – 5 min | 19 – 22 min |

What is claimed is:

1. In a method for preparation of a hard gelatin capsule disintegrating in about 2 to about 22 minutes, said capsule containing a measured dose of midecamycin antibiotic as a medicine for delivery to the stomach when said capsule is ingested orally, said medicine otherwise tending in time to retard the disintegration of said hard gelatin capsule to 19 to 21 minutes, the improvement wherein the increase in the hard gelatin capsule disintegration time with capsule age is at least partially arrested, and improved stability of the disintegration time, to within 2 to 6 minutes, is achieved, which comprises incorporating into said capsule at least about 25 parts by weight of a pharmaceutically acceptable additive consisting essentially of casein per 70 parts by weight of midecamycin.

* * * * *